United States Patent
Hembre et al.

(10) Patent No.: US 9,573,078 B2
(45) Date of Patent: *Feb. 21, 2017

(54) QUATERNARY CARBOXYLATE COMPOSITIONS FOR EXTRACTING $C_1$ TO $C_4$ CARBOXYLIC ACIDS FROM AQUEOUS STREAMS

(71) Applicant: Eastman Chemical Company, Kingsport, TN (US)

(72) Inventors: Robert Thomas Hembre, Johnson City, TN (US); Scott Donald Barnicki, Kingsport, TN (US); Chester Wayne Sink, Kingsport, TN (US); Christopher Hardacre, Belfast (GB); Jingyi Liu, Shantou (CN); Fei Qi, Belfast (GB)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/973,812

(22) Filed: Dec. 18, 2015

(65) Prior Publication Data

US 2016/0175737 A1    Jun. 23, 2016

Related U.S. Application Data

(60) Provisional application No. 62/094,238, filed on Dec. 19, 2014.

(51) Int. Cl.
*B01D 11/04* (2006.01)
*C07C 51/44* (2006.01)
*C07C 51/48* (2006.01)
*C07F 9/54* (2006.01)
*C07F 9/30* (2006.01)

(52) U.S. Cl.
CPC ........... *B01D 11/0492* (2013.01); *C07C 51/44* (2013.01); *C07C 51/48* (2013.01); *C07F 9/301* (2013.01); *C07F 9/5407* (2013.01)

(58) Field of Classification Search
CPC ..... B01D 11/0492; C07C 51/44; C07C 51/48; C07F 9/5407; C07F 9/301
See application file for complete search history.

(56) References Cited

U.S. PATENT DOCUMENTS

| | | |
|---|---|---|
| 1,839,894 A | 1/1932 | Ricard et al. |
| 1,860,512 A | 5/1932 | Ricard et al. |
| 1,861,841 A | 6/1932 | Clarke et al. |
| 1,917,391 A | 7/1933 | Othmer |
| 2,028,800 A | 1/1936 | Othmer |
| 2,050,234 A | 8/1936 | Othmer |
| 2,063,940 A | 12/1936 | Martin |
| 2,076,184 A | 4/1937 | Othmer |
| 2,123,348 A | 7/1938 | Wentworth |
| 2,157,143 A | 5/1939 | Othmer |
| 2,184,563 A | 12/1939 | Othmer |
| 2,199,983 A | 5/1940 | Bright |
| 2,204,616 A | 6/1940 | Dthmer |
| 2,269,163 A | 1/1942 | Othmer |
| 2,275,802 A | 3/1942 | Othmer |
| 2,275,862 A | 3/1942 | Othmer |
| 2,317,758 A | 4/1943 | Guinot |
| 2,333,756 A | 11/1943 | Wenthworth |
| 2,384,374 A | 9/1945 | Harrison |
| 2,395,010 A | 2/1946 | Othmer |
| 2,537,658 A | 1/1951 | Dornte |
| 2,567,244 A | 9/1951 | Solomon |
| 2,854,385 A | 9/1958 | Alheritiere |
| 2,859,154 A | 11/1958 | Othmer |
| 3,052,610 A | 9/1962 | Akaboshi et al. |
| 3,816,524 A | 6/1974 | Grindstead |
| 4,909,939 A | 3/1990 | Rickelton |
| 5,662,780 A | 9/1997 | Sasaki et al. |
| 5,663,422 A | 9/1997 | Perri et al. |
| 7,435,318 B2 | 10/2008 | Arlt et al. |
| 7,709,168 B2 | 5/2010 | Wu et al. |
| 7,812,191 B2 | 10/2010 | Hallinan et al. |
| 7,858,678 B2 | 12/2010 | Avakian et al. |

(Continued)

FOREIGN PATENT DOCUMENTS

| | | |
|---|---|---|
| DE | 3035641 A1 | 5/1982 |
| EP | 1 645 577 A1 | 4/2006 |

(Continued)

OTHER PUBLICATIONS

Q. Yang et al., "Long-Chain Fatty Acid-Based Phosphonium Ionic Liquids with Strong Hydrogen-Bond Basicity and Good Lipophilicity: Synthesis, Characterization, and Application in Extraction," ACS Sustainable Chem. Eng., vol. 3, pp. 309-316 (2015).

K. Park et al., "Ionic Liquids as Plasticizers/Lubricants for Polylactic Acid," Polymer Eng. and Sci., vol. 50, pp. 1105-1110 (2009).

A. Rosatella et al., "Studies on dissolution of carbohydrates in ionic liquids and extraction from aqueous phase," Green Chem., vol. 11, pp. 1406-1413 (2009).

M. Selva et al., "Carbonate, acetate and phenolate phosphonium salts as catalysts in transesterification reactions for he synthesis of non-symmetric dialkyl carbonates," Org. Biomol. Chem., vol. 10, pp. 6569-6578 (2012).

V. Shaturin et al., "Tetraphenylphosphonium Carboxylates and Sulfonates. Synthesis and Structure," Russian J. Gen. Chem., vol. 79, pp. 78-87 (2009).

(Continued)

*Primary Examiner* — Shailendra Kumar
(74) *Attorney, Agent, or Firm* — Phan Law Group PLLC

(57) ABSTRACT

This invention relates to solvents for extracting $C_1$ to $C_4$ carboxylic acids from aqueous streams. More specifically, the extraction solvents include one or more salts composed of a tetraalkylphosphonium cation and a carboxylate anion. The extraction solvents may further include one or more non-ionic liquid organic solvents as an enhancer. The extraction solvents are useful for extracting aqueous mixtures containing one or more lower carboxylic acids, such as monocarboxylic acids, alkoxycarboxylic acids, and halogen-containing carboxylic acids.

30 Claims, 1 Drawing Sheet

(56) References Cited

U.S. PATENT DOCUMENTS

| | | | |
|---|---|---|---|
| 8,540,900 | B2 | 9/2013 | Foley et al. |
| 8,674,050 | B2 | 3/2014 | Spyrou |
| 2012/0138789 | A1 | 6/2012 | Del Sesto et al. |
| 2014/0076805 | A1 | 3/2014 | Massingill |
| 2014/0275597 | A1 | 9/2014 | Zhang et al. |

FOREIGN PATENT DOCUMENTS

| | | |
|---|---|---|
| EP | 2 530 066 A1 | 12/2012 |
| JP | 2014-40389 A | 3/2014 |
| WO | 02/079212 A1 | 10/2002 |
| WO | 03/020843 A1 | 3/2003 |
| WO | 2006/007703 A1 | 1/2006 |
| WO | 2014/060651 A1 | 4/2014 |

OTHER PUBLICATIONS

A. Holding et al., "Amphiphilic and Phase-Separable Ionic Liquids for Biomass Processing," ChemSusChem, vol. 7, pp. 1422-1434 (2014).
M. Blesic et al., "Solubility of alkanes, alkanols and their fluorinated counterparts in tetraalkylphosphonium ionic liquids," Phys. Chem. Chem. Phys., vol. 12, pp. 9685-9692 (2010).
Y. Zhou et al., "Ionic Liquids Composed of Phosphonium Cations and Organophosphate, Carboxylate, and Sulfonate Anions as Lubricant Antiwear Additives," Langmuir, vol. 30, pp. 13301-13311 (2014).
C. Neves et al., "Separation of ethanol-water mixtures by liquid-liquid extraction using phosphonium-based ionic liquids," Green Chem., vol. 13, pp. 1517-1526 (2011).
F. Vicente et al., "Design of novel aqueous micellar two-phase systems using ionic liquids as co-surfactants for the selective extraction of (bio)molecules," Sep. and Purif. Tech., vol. 135, pp. 259-267 (2014).
A. Grijalba et al., "Capabilities of several phosphonium ionic liquids for arsenic species determination in water by liquid-liquid microextraction and electrothermal atomic absorption spectrometry," Anal. Methods, vol. 7, pp. 490-499 (2015).
P. Dallas et al., "Self-suspended permanent magnet FePt ferrofluids," J. Colloid and Interface Sci., vol. 407, pp. 1-7 (2013).
G. Yadav et al., "Ionic Liquid as Catalyst for Solid-Liquid Phase Transfer Catalyzed Synthesis of p-Nitrodiphenyl Ether," Ind. Eng. Chem. Res., vol. 47, pp. 9081-9089 (2008).
F. Oliveira et al., "Extraction of 1-lactic,l-malic, and succinic acids using phosphonium-based ionic liquids," Sep. and Purif. Tech., vol. 85, pp. 137-146 (2012).
Int'l Search Report and Written Opinion issued in Int'l Application No. PCT/US2015/066571.
J. Martak et al., "Phosphonuim Ionic Liquids as New, Reactive Extractants of Lactic Acid," Chem. Papers, vol. 60, pp. 395-398 (2006).
M. Blahusiak et al., "New approach to regeneration of an ionic liquid containing solvent by molecular distillation," Chem. Papers, vol. 65, pp. 603-607 (2011).
Y. Jiang et al., "Enzymatic Hydrolysis of Penicillin for 6-APA Production in Three-Liquid-Phase System," Applied Biochem. Biotech., vol. 144, pp. 145-159 (2008).
G. Nemeth et al., "Asymmetric lactic acid esterification with biocatalysts in ionic liquid," Hungarian J. Indus. Chem., vol. 39, pp. 419-425 (2011).
B. Major et al., "Microwave assisted enzymatic esterification of lactic acid and ethanol in phosphonium type ionic liquids as co-solvents," Green Chem., vol. 11, pp. 614-616 (2009).
Int'l Search Report and Written Opinion issued in Int'l Application No. PCT/US2015/066572.

Hembre et al., Copending U.S. Appl. No. 14/973,817, filed Dec. 18, 2015.
Liu et al., Copending U.S. Appl. No. 14/973,826, filed Dec. 18, 2015.
A. Stojanovic et al., "Phosphonium and Ammonium Ionic Liquids with Aromatic Anions: Synthesis, Properties, and Platinum Extraction," Aust. J. Chem., vol. 63, pp. 511-524 (2010).
G. Cui et al., "Tuning Anion-Functionalized Ionic Liquids for Improved SO2 Capture," Agnew. Chem. Int. Ed., vol. 52, pp. 10620-10624 (2013).
G. Cui et al., "Tuning the Basicity of Cyano-Containing Ionic Liquids to Improve SO2 Capture through Cyano-Sulfur Interactions," Chem. Eur. J., vol. 21, pp. 5632-5639 (2015).
S. Das et al., "Ionic liquid-based fluorescien colorimetric pH nanosensors," RSC Adv., vol. 3, pp. 21054-21061 (2013).
S. Murugesan et al., "Benzoate-based room temperature ionic liquids—thermal properties and glycosaminoglycan dissolution," Carbohydrate Polymers, vol. 63, pp. 268-271 (2006).
J. McFarlane et al., "Room Temperature Ionic Liquids for Separating Organics from Produced Water," Separation Sci. and Tech., vol. 40, pp. 1245-1265 (2005).
Int'l Search Report and Written Opinion issued in Int'l Application No. PCT/US2015/066575.
Eaglesfield et al., "Recovery of Acetic Acid from Dilute Aqueous Solutions by Liquid-Liquid Extraction—Part 1," The Industrial Chemist, vol. 29, pp. 147-151 (1953).
King, "Amine-Based Systems for Carboxylic Acid Recovery: Tertiary Amines and the Proper Choice of Diluent Allow Extraction and Recovery from Water," CHEMTECH, vol. 5, pp. 285-291 (1992).
Tamada et al., "Extraction of Carboxylic Acids with Amine Extractants. 2. Chemical Interactions and Interpretation of Data," Ind. Eng. Chem. Res., vol. 29, pp. 1327-1333 (1990).
Blahusiak et al., "Extraction of butyric acid with a solvent containing ammonium ionic liquid," Sep. Purif. Technol., vol. 119, pp. 102-111 (2013).
Poole et al., "Extraction of Organic Compounds with Room Temperature Ionic Liquids," J. Chromatogr. (A), vol. 1217, pp. 2268-2286 (2010).
Bradaric et al., "Industrial Preparation of Phosphonium Ionic Liquids", Green Chem., vol. 5, pp. 143-152 (2003).
Matsumoto et al., "Extraction of Organic Acids Using Imidazolium-Based Ionic Liquids and Their Toxicity to Lactobacillus rhamnosus," Sep. Purif. Technol., vol. 40, pp. 97-101 (2004).
Cieniecka-Roslonkiewicz et al., "Synthesis, anti-microbial activities and anti-electrostatic properties of phosphonium-based ionic liquids," Green Chem., vol. 7, pp. 855-862 (2005).
Kogelnig et al., "Greener Synthesis of New Ammonium Ionic Liquids and their Potential as Extracting Agents," Tetrahedron Letters, vol. 49, pp. 2782-2785 (2008).
Ferguson et al., "A Greener, Halide-Free Approach to Ionic Liquid Synthesis," Pure & Appl. Chem., vol. 84, pp. 723-744 (2012).
Wardell et al., "Solvent Equilibria for Extraction of Carboxylic Acids from Water," J. Chem. Eng. Data, vol. 23, No. 2, pp. 144-148 (1978).
Rocha et al., "Extraction of Volatile Fatty Acids Using Nature Based Ionic Liquids," Proceedings of the 20th European Conference on Thermophysical Properties (ECTP), Aug. 31-Sep. 4, Porto, Portugal, pp. 1-7 (2014).
Martak et al., "Ionic Liquids in Pertraction and Extraction of Organic Acids," XIX-th Ars Separatoria, Zloty Potok, Poland, pp. 106-113 (2004).
Martak et al., "Screening of ionic liquids for application in solvent extraction and pertration," 31th Int'l Conf. SSCHE, Tatranske Matliare, Slovakia, p. 188 (2004).
Martak et al., "Liquid-liquid equilibria of butyric acid for solvents containing a phosphonium ionic liquid," Chem. Papers, vol. 62, pp. 42-50 (2008).
Martak et al., "Extraction of Lactic Acid by Phosphonium Ionic Liquids," Sep. Purif. Technol., vol. 57, pp. 483-494 (2007).

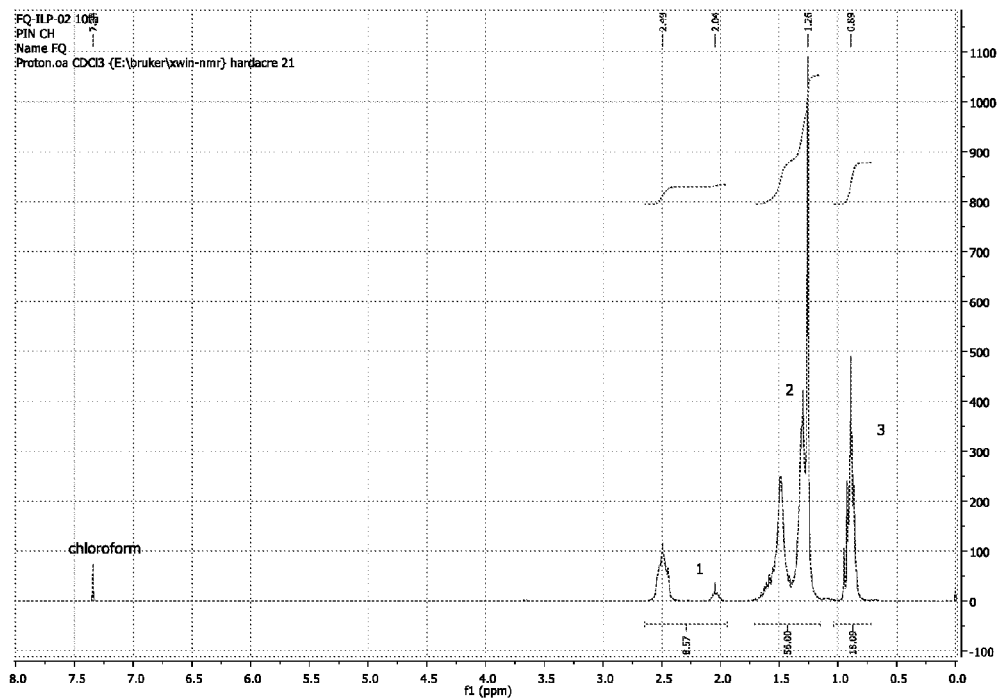

QUATERNARY CARBOXYLATE COMPOSITIONS FOR EXTRACTING $C_1$ TO $C_4$ CARBOXYLIC ACIDS FROM AQUEOUS STREAMS

CROSS-REFERENCE TO RELATED APPLICATION

This application claims the benefit of Provisional Application No. 62/094,238 filed on Dec. 19, 2014 under 35 U.S.C. §119(e)(1); the entire content of the provisional application is hereby incorporated by reference.

FIELD OF THE INVENTION

The invention generally relates to solvents for extracting $C_1$ to $C_4$ carboxylic acids from aqueous streams, compositions containing the same, and processes for separating the acids from water.

BACKGROUND OF THE INVENTION

The recovery of $C_1$ to $C_4$ carboxylic acids (hereinafter "lower acids") from aqueous streams is a common industrial problem arising from a variety of reaction and processing steps. Simple distillation of wet acid streams to recover glacial acids is hampered by unfavorable vapor-liquid equilibrium (VLE) and high energy costs with all $C_1$ to $C_4$ carboxylic acids. Examples of unfavorable VLE include the formic acid-water maximum-boiling homogeneous azeotrope, the acetic acid-water VLE "pinch" (a region of low relative volatility), and the minimum-boiling homogeneous azeotropes with water and all $C_3$-$C_4$ carboxylic acids.

Various approaches have been suggested in the art to address the problem of lower acid recovery from wet acid feeds. For example, one approach subjects an aqueous lower acid solution to azeotropic distillation together with an entraining component capable of forming a heterogeneous minimum-boiling azeotrope with water, so that the azeotrope boils at a temperature substantially lower than pure water, the pure lower acid, and any acid-water azeotrope. An extraction step often precedes the azeotropic distillation. The extraction step partitions the carboxylic acid into a water-immiscible solvent (which is often the same as the azeotropic entrainer) in order to remove the bulk of the water from the recovered acid. Many examples of azeotropic distillation, extraction, and combinations thereof using conventional organic solvents have been proposed in the art. These include U.S. Pat. Nos. 1,839,894; 1,860,512; 1,861,841; 1,917,391; 2,028,800; 2,050,234; 2,063,940; 2,076,184; 2,123,348; 2,157,143; 2,184,563; 2,199,983; 2,204,616; 2,269,163; 2,275,834; 2,275,862; 2,275,867; 2,317,758; 2,333,756; 2,359,154; 2,384,374; 2,395,010; 2,537,658; 2,567,244; 2,854,385; 3,052,610; and 5,662,780, and Eaglesfield et al., "Recovery of Acetic Acid from Dilute Aqueous Solutions by Liquid-Liquid Extraction—Part 1," The Industrial Chemist, Vol. 29, pp. 147-151 (1953).

Several solvent characteristics determine the capital and energy costs of extraction-distillation processes for the extractive recovery of lower acids from wet acid feeds. The solvent for the extraction process is immiscible with water and meets two criteria:

a) The solvent shows some selectivity between extraction of the carboxylic acid and water, i.e., the ratio of carboxylic acid to water in the extraction solvent after extraction is substantially larger than in the wet acid feed stream. This factor can be quantified as the weight ratio of water to acid in the extract stream as defined in more detail below.

b) The solvent shows sufficient affinity and capacity for the lower carboxylic acid.

These characteristics are quantifiable from experimentally determined equilibrium partition coefficients as defined in more detail below.

The equilibrium partition coefficient (also used interchangeably with the term "partition coefficient") for component A (the lower carboxylic acid) is defined as follows:

$$P(A) = \frac{\text{weight percent } A \text{ in solvent phase}}{\text{weight percent } A \text{ in aqueous phase}}$$

The partition coefficient is a measure of the relative concentrations of the solute to be extracted in the two phases. The value of the acid partition coefficient is directly related to the amount of solvent that is required to effect a given extraction. Low values of the partition coefficient indicate high levels of solvent are required, and high values of the partition coefficient indicate low levels of solvent are required. Since the acid partition coefficient changes with acid concentration, the minimum amount of solvent required to effect a given amount of acid extraction also changes. Thus, the controlling solvent flow requirement for the extraction is dictated by the lowest value of the acid partition coefficient as the acid concentration varies from the high of the inlet wet acid feed to the low of the outlet acid concentration of the exiting raffinate stream.

The controlling acid partition coefficient may be defined as:

$$P_{cont} = \text{minimum}(P_{raff}, P_{extr})$$

where $P_{raff}$=acid partition coefficient at an acid concentration approaching that desired in the raffinate stream (i.e., at low acid concentration); and $P_{extr}$=acid partition coefficient at an acid concentration approaching that desired in the extract stream (i.e., at high acid concentration).

The most important water-acid selectivity value is that at the extract end of the extraction cascade. It is defined as:

$$R_{extr} = W_{extr}/A_{extr}$$

where $W_{extr}$=weight fraction of water in the extract product stream; and $A_{extr}$=weight fraction of acid in the extract product stream.

The controlling partition coefficient, $P_{cont}$, and extract water-to-acid ratio, $R_{extr}$, may be combined to yield an overall extraction factor, $\epsilon$, which is a simple measure of the efficacy of a given solvent for recovering lower acids from wet acid feeds in an extraction-distillation process. The extraction factor, $\epsilon$, is defined as:

$$\epsilon = P_{cont}/R_{extr} = (P_{cont} * A_{extr})/W_{extr}$$

Generally, the higher the extraction factor, the lower the capital and energy costs are for a given extraction.

Extraction solvents that exhibit the inverse behavior are also known. That is, their acid partition coefficient is lowest at the extract end of the cascade (high acid concentration) and highest at the raffinate end (low acid concentration). Examples of such solvents include nitriles, phosphate esters, phosphine oxides (U.S. Pat. Nos. 3,816,524 and 4,909,939), and amines (e.g., King, "Amine-Based Systems for Carboxylic Acid Recovery: Tertiary Amines and the Proper Choice of Diluent Allow Extraction and Recovery from Water," CHEMTECH, Vol. 5, pp. 285-291 (1992); and Tamada et al., "Extraction of Carboxylic Acids with Amine Extractants. 2. Chemical Interactions and Interpretation of Data," *Ind. Eng. Chem. Res.*, Vol. 29, pp. 1327-1333 (1990)).

This inverse behavior (partition coefficient highest at low acid concentration) has also been observed for a phosphonium- and an ammonium-phosphinate ionic liquid (Blauser et al., "Extraction of butyric acid with a solvent containing ammonium ionic liquid," *Sep. Purif. Technol.*, Vol. 119, pp. 102-111 (2013); Martak et al., "Phosphonium ionic liquids as new, reactive extractants of lactic acid," *Chem. Papers*, Vol. 60, pp. 395-98 (2006)) and a phosphonium carboxylate salt (Oliveira et al., "Extraction of L-Lactic, L-Malic, and Succinic Acids Using Phosphonium-Based Ionic Liquids," *Sep. Purif. Tech.*, Vol. 85, pp. 137-146 (2012)). Oliveira et al., in particular, report that $P_{666,14}$-decanoate fails to form a simple two-phase system in the majority of extraction trials with lactic, succinic, and malic acids. A third phase complicates the distribution and recovery of carboxylic acid.

The use of hydrophobic ionic liquids as extraction solvents has been reviewed by Poole et al., "Extraction of Organic Compounds with Room Temperature Ionic Liquids," *J. Chromatogr. (A)*, Vol. 1217, pp. 2268-2286 (2010). The development and advantages of phosphonium ionic liquids have been reviewed by Robertson et al., "Industrial Preparation of Phosphonium Ionic Liquids", *Green Chem.*, Vol. 5, pp. 143-152 (2003)), and their application to the extraction of ethanol from fermentation broths is addressed by Neves et al., "Separation of Ethanol-Water Mixtures by Liquid-Liquid Extraction Using Phosphonium-Based Ionic Liquids," *Green Chem.*, Vol. 13, pp. 1517-1526 (2011).

Extraction of lower carboxylic acids using imidazolium and phosphonium ionic liquids has also been reported. For acetic acid, McFarlane et al. report on bmim-$NTf_2$, omim-$NTf_2$, bmim-$PF_6$, $P_{666,14}$-LABS/nonanol, $P_{444,14}$-LABS/nonanol, and $P_{666,14}$-$OSO_2Me$ ("Room Temperature Ionic Liquids for Separating Organics from Produced Waters," *Sep. Sci. & Tech.*, Vol 40, 1245-1265 (2005)). Hashikawa claims $P_{222,8}$-$NTf_2$ for acetic, propionic, and butyric acids ("Method for Producing Acetic Acid," JP 2014/40389, Daicel, (Mar. 6, 2014)). And Matsumoto et al. report on bmim-$PF_6$, hmim-$PF_6$, and omim-$PF_6$ ("Extraction of Organic Acids Using Imidazolium-Based Ionic Liquids and Their Toxicity to *Lactobacillus rhamnosus*," *Sep. and Purif. Tech.*, Vol. 40, pp. 97-101 (2004)).

None of these documents, however, employed a quaternary phosphonium carboxylate with mono-functional carboxylic acids. Moreover, lower carboxylic acid partitioning was poor in the reports by McFarlane, Hashikawa, and Matsumoto. Furthermore, adding an alcohol to phosphonium ionic liquid compositions for extracting lower carboxylic acids is recognized by those skilled in the art as not being preferred, due to the formation of carboxylic ester derivatives of the alcohols with the acid extracts, especially in downstream distillation or evaporative processes for purifying the lower carboxylic acids. This exclusion is addressed by Judson King, "Acetic Acid Extraction," *Handbook of Solvent Extraction*, Krieger Publ. Co. (1991).

Hashikawa, in particular, claims only using ionic liquids with fluorine-containing anions, such as bis(fluorosulfonyl)imide, bis(fluoroalkylsulfonyl)imides, tris(perfluoroalkyl)trifluorophosphates, hexafluorophosphates, tetrafluoroborates, and perfluoroalkylsulfonates. These anions add significant cost and toxicity concerns to large-scale applications. In addition, Hashikawa claims ionic liquids with phosphonium salts containing a total of only ten carbon atoms or higher. According to the data presented in the Hashikawa application, triethyl(octyl)phosphonium bis(trifluoromethylsulfonyl)-imide exhibits relatively poor extraction behavior for acetic acid, with a small two-phase region, low capacity for acetic acid, and very low partition coefficients (between about 0.06 and 0.1).

Despite the poor performance of the above reported and claimed ionic liquid systems, the extremely low vapor pressure of ionic liquids remains an attractive physical property for a lower-carboxylic-acid-extracting phase. Thus, there is a need in the art for an extraction solvent with excellent partitioning of lower carboxylic acids from aqueous solutions and that enables the simple separation of these acids via distillation from the solvent. There is also a need for extraction solvents with high extraction factors whereby $C_1$ to $C_4$ carboxylic acids can be recovered from wet acid feeds in an energy-efficient and cost-effective manner.

The present invention addresses these needs as well as others, which will become apparent from the following description and the appended claims.

SUMMARY OF THE INVENTION

The invention is as set forth in the following detailed description and the appended claims.

Briefly, in one aspect, the present invention provides a solvent for extracting a $C_1$ to $C_4$ carboxylic acid from water. The extraction solvent comprises (a) a quaternary phosphonium carboxylate salt and (b) a non-ionic organic solvent with the proviso that the non-ionic organic solvent is not the extract. The carboxylate salt has the general formula 1:

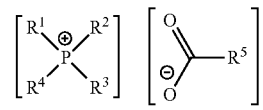

wherein $R^1$, $R^2$, $R^3$ and $R^4$ are each independently a $C_1$ to $C_{26}$ hydrocarbyl group, provided that $R^1$, $R^2$, $R^3$, and $R^4$ collectively have a total of at least 24 carbon atoms; and $R^5$ is hydrogen or a $C_1$ to $C_{24}$ non-aromatic hydrocarbyl group.

In another aspect, the present invention provides a composition for separating a $C_1$ to $C_4$ carboxylic acid from water. The composition comprises:

(a) a quaternary phosphonium carboxylate salt according to the invention;

(b) a non-ionic organic solvent according to the invention;

(c) a $C_1$ to $C_4$ carboxylic acid; and (d) water.

In yet another aspect, the present invention provides a process for separating a $C_1$ to $C_4$ carboxylic acid from water. The process comprises contacting a feed mixture comprising a $C_1$ to $C_4$ carboxylic acid and water with an extraction solvent according to the invention at conditions effective to form (a) an extract mixture comprising the carboxylate salt, the non-ionic organic solvent, and at least a portion of the $C_1$ to $C_4$ carboxylic acid from the feed mixture and (b) a raffinate mixture comprising water and less of the $C_1$ to $C_4$ carboxylic acid compared to the feed mixture.

In one embodiment, the present invention is directed to a process for separating acetic acid from water. The process comprises contacting a feed mixture comprising acetic acid and water with an extraction solvent comprising a quaternary phosphonium carboxylate salt according to the invention at conditions effective to form (a) an extract mixture comprising the carboxylate salt and at least a portion of the acetic acid from the feed mixture and (b) a raffinate mixture comprising water and less of the acetic acid compared to the feed mixture.

BRIEF DESCRIPTION OF THE DRAWING

The FIGURE is an 1H NMR spectrum of $P_{666,14}$-2EH in $CDCl_3$ at 300 MHz from Example 2.

DETAILED DESCRIPTION OF THE INVENTION

It has been found, surprisingly, that when certain quaternary phosphonium carboxylates are combined with aqueous solutions of a lower carboxylic acid, the resulting partitioning of the lower acid into the phosphonium carboxylate phase can be fairly high, particularly when the concentration of the lower acid is low (e.g., <5 wt %). The carboxylates show superior selectivity for lower acid extraction over co-extraction of water. As a result, the extraction factor, $\epsilon$, is significantly higher for the carboxylates than other classes of lower acid extraction solvents, and are thus particularly useful for recovering lower acids from wet acid streams.

Accordingly, in one aspect, the present invention provides quaternary phosphonium carboxylates that are useful for separating lower acids from aqueous streams. The carboxylates are depicted by the general formula 1:

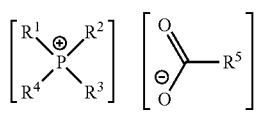

1 wherein $R^1$, $R^2$, $R^3$ and $R^4$ are each independently a $C_1$ to $C_{26}$ hydrocarbyl group, provided that $R^1$, $R^2$, $R^3$, and $R^4$ collectively have a total of at least 24 carbon atoms; and $R^5$ is hydrogen or a $C_1$ to $C_{24}$ non-aromatic hydrocarbyl group.

As used herein, the term "hydrocarbyl" refers to a group containing hydrogen and carbon atoms, and may be straight-chained or branched, cyclic or acyclic, and saturated or unsaturated.

Each of $R^1$, $R^2$, $R^3$, and $R^4$ may have the same number of carbon atoms or may be of different lengths. In one embodiment, $R^1$, $R^2$, $R^3$, and $R^4$ collectively have not more than 54 carbon atoms. In another embodiment, each of $R^1$, $R^2$, $R^3$, and $R^4$ has at least 6 carbon atoms. In other embodiments, each of $R^1$, $R^2$, $R^3$, and $R^4$ contains from 6 to 24 carbon atoms, 6 to 20 carbon atoms, 6 to 18 carbon atoms, 6 to 14 carbon atoms, or 8 to 14 carbon atoms.

Preferably, $R^5$ has such a length that when combined with the phosphonium group $[PR^1R^2R^3R^4]$, defined as above, the carboxylate anion renders the salt hydrophobic. In one embodiment, $R^5$ is a $C_3$ to $C_9$ non-aromatic hydrocarbyl group. In another embodiment, $R^5$ is a $C_3$ to $C_{20}$ non-aromatic hydrocarbyl group. In other embodiments, $R^5$ may contain from 1 to 20 carbon atoms, 1 to 18 carbon atoms, 1 to 16 carbon atoms, 1 to 14 carbon atoms, 1 to 12 carbon atoms, 3 to 20 carbon atoms, 3 to 18 carbon atoms, 3 to 16 carbon atoms, 3 to 14 carbon atoms, or 3 to 12 carbon atoms. $R^5$ may contain functional groups such as alkoxy, olefinic, and halogen functionalities.

By "hydrophobic," it is meant that the salt is immiscible in water at typical extraction conditions, e.g., has less than 5 wt % miscibility in water at 20° C.

The carboxylate salt is the liquid state under typical extraction conditions.

Examples of phosphonium carboxylates having the structure of formula 1 are listed in Table 1 below. Their CAS registry numbers are also listed if the compounds are known.

TABLE 1

CAS Registry Numbers of Some Known Phosphonium Carboxylates

| Anion | Cation | | |
|---|---|---|---|
| | $P_{6666}$ | $P_{666,14}$ | $P_{8888}$ |
| formate | 1393375-35-3[a] | 1319099-97-2[a] | 1393375-36-4[a] |
| acetate | 49720-18-5[a] | 872700-58-8[a] | 172682-89-2[c] |
| propionate | NF | 1393375-55-7[a] | NF |
| acrylate | NF | NF | NF |
| butyrate | NF | 1393375-56-8[a] | NF |
| isobutyrate | NF | 1393375-59-1[a] | NF |
| methacrylate | NF | NF | NF |
| hexanoate | NF | 151196-58-0[a] | NF |
| 2-ethylbutyrate | NF | NF | NF |
| octanoate | NF | 1393375-58-0[a] | NF |
| 2-ethylhexanoate | NF | NF | NF |
| nonanoate | NF | NF | NF |
| decanoate | NF | 465527-65-5[b] | NF |

[a]*Pure & Appl. Chem.*, Vol. 84, p. 723 (2012).
[b]*Green Chem.*, Vol. 7, p. 855 (2005).
[c]U.S. Pat. No. 5,663,422 (Eastman Chemical; 1997).
NF = not found.

The carboxylate derivatives in Table 1 that do not have CAS registration numbers are previously unknown and, thus, are specifically contemplated as being within the scope of the present invention.

Mixtures containing more than one quaternary cation and more than one carboxylate anion are also useful for the extraction of lower acids from aqueous solutions and, therefore, are also contemplated as being within the scope of the present invention.

In one embodiment, the carboxylate salt comprises a tetraalkylphosphonium salt of formic acid, acetic acid, propionic acid, n-butyric acid, isobutyric acid, n-valeric acid, isovaleric acid, n-hexanoic acid, 2-ethylbutyric acid, heptanoic acids, n-octanoic, 2-ethylhexanoic acid, nonanoic acid, decanoic acid, dodecanoic acid, palmitic acid, stearic acid, oleic acid, linolenic acid, mixed vegetable-derived acids, or chloroacetic acid.

In another embodiment, the carboxylate salt comprises a trihexyl(tetradecyl)phosphonium salt of formic acid, acetic acid, propionic acid, n-butyric acid, isobutyric acid, n-valeric acid, isovaleric acid, n-hexanoic acid, 2-ethylbutyric acid, heptanoic acid, n-octanoic, 2-ethylhexanoic acid, nonanoic acid, decanoic acid, dodecanoic acid, palmitic acid, stearic acid, oleic acid, linolenic acid, mixed vegetable-derived acids, or chloroacetic acid.

In a further embodiment, the carboxylate salt comprises trihexyl(tetradecyl)phosphonium carboxylate. The carboxylate anion may selected from the group consisting of formate, acetate, propionate, acrylate, butyrate, isobutyrate, methacrylate, hexanoate, 2-ethylbutyrate, octanoate, 2-ethylhexanoate, nonanoate, and decanoate.

Some phosphonium carboxylates having the structure of formula 1 are commercially available, while others may be produced by known methods from readily available precursors. See, e.g., Kogelnig et al., "Greener Synthesis of New Ammonium Ionic Liquids and their Potential as Extracting Agents," *Tetrahedron Letters*, Vol. 49, pp. 2782-2785 (2008) and Ferguson et al., "A Greener, Halide-Free Approach to Ionic Liquid Synthesis," *Pure & Appl. Chem.*, Vol. 84, pp. 723-744 (2012)). The former approach involves the metathesis of an alkali carboxylate with a quaternary ammonium halide, while the latter approach employs an ion-exchange resin and in our experience (see Examples 1 and 2 below) produces ionic liquids with lower amounts of residual halide. An example of a readily available precursor is trihexyl(tetradecyl)phosphonium chloride.

So while synthetic methods of a general nature are known for making quaternary phosphonium carboxylates, a relatively small number have been prepared and their application to the extraction of low acids from aqueous streams is unknown, with one exception as reported by Oliveira et al. and described herein: $P_{66614}$-decanoate for the extraction of lactic, malic, and succinic acids. In one embodiment, therefore, the invention excludes the use of $P_{666,14}$-decanoate alone for extracting aqueous solutions of lactic, malic, or succinic acids.

In a second aspect, the invention provides a composition A:

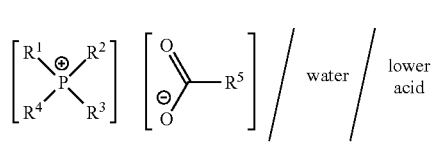

Composition A represents a unique biphasic mixture comprising a quaternary phosphonium carboxylate according to the general formula 1, a lower acid, and water. Other species may also be present. Composition A is useful for separating the lower acid from water.

As noted above, lower acids refer to $C_1$ to $C_4$ carboxylic acids. By way of example, the carboxylic acids may be monocarboxylic acids, alkoxycarboxylic acids, or halogen-containing carboxylic acids. Examples of such acids include formic acid, acetic acid, propionic acid, acrylic acid, n-butyric acid, isobutyric acid, methacrylic acid, chloroacetic acid, dichloroacetic acid, trichloroacetic acid, trifluoroacetic acid, methoxyacetic acid, and the like. In one embodiment, the $C_1$ to $C_4$ carboxylic acid is a monocarboxylic acid without a hydroxyl group.

Examples of processes that produce diluted aqueous carboxylic acid-containing streams (i.e., comprising less than 1 weight percent to 60 weight percent of $C_1$ to $C_4$ carboxylic acids in an aqueous mixture, which may be referred to as "wet acid feeds") include the production of cellulose esters or terephthalic acid, the production of ketene or higher ketenes from high temperature dehydration of carboxylic acids and anhydrides, the hydrolysis of poly(vinylacetate), the production of Fischer-Tropsch liquids, oil and gas production (yielding "produced waters"), the ketonization of carboxylic acids to ketones, the oxidation of ethylene to acetaldehyde by the Wacker process, the oxidation of propylene to acrylic acid, the oxidation of oxo aldehydes to their carboxylic acids, hydrocarboxylation of formaldehyde with water and carbon monoxide, the oxidation of isobutylene to methacrylic acid, pyroligneous acids, fermentations broths, vinegar streams, and the like. Vinegar streams refer to aqueous streams containing acetic acid. In one embodiment, the wet acid feed is derived from the production of cellulose esters.

The wet acid feed may comprise from 0.5 to 60 weight percent of one or more of the $C_1$ to $C_4$ carboxylic acids. More preferably, the wet acid feed comprises 0.5 to 35 weight percent of the $C_1$ to $C_4$ carboxylic acids. Because of the unusually high acid partition coefficients of the carboxylate salts of the invention even at low acid concentrations, the extraction solvent of the instant invention may be used advantageously to extract lower acids at concentrations as low as 0.5 weight percent in the wet acid feed.

As used herein, the terms "feed" and "feed mixture" are intended to have their commonly understood meaning in the liquid-liquid extraction art, which is the solution that contains the materials to be extracted or separated. In the present invention, one example of a "feed" is a mixture composed of one or more of formic, acetic, propionic, acrylic, n-butyric, isobutyric, methacrylic, methoxyacetic, chloroacetic, dichloroacetic, trichloroacetic, and trifluoroacetic acids in water. In the present invention, the terms "feed" and "feed mixture" are synonymous with "aqueous acid stream," "weak acid stream," and "wet acid feed."

The term "extraction solvent," as used herein, is intended to be synonymous with the term "extractant" and is intended to mean the water-immiscible or hydrophobic liquid that is used in the extraction process to extract materials or solutes from the feed.

The weight ratio of carboxylate to wet acid feed in composition A may vary over a wide range. For example, the ratio may range from 0.2 to 10:1 or, more preferably, from 0.3 to 4:1.

A feature of composition A is that it separates into two phases, an aqueous and an organic phase, with the lower acid distributed between them. The biphasic nature of composition A is desirable in order to physically separate the lower acid from the aqueous solution. The amount of lower acid distributed between the phases is only limited by the biphasic property of the system. Preferably, the lower acid amount does not exceed a level at which the biphasic nature of the composition is lost. Likewise, other materials may also be present, but only to the extent that the biphasic nature of the system is retained. Complex systems that form more than two phases are not preferred, since such a system can obscure the effective separation of the lower acid.

Quaternary phosphonium carboxylates that form greater than two-phase systems, emulsions, or other complex mixtures may be simplified by adding a hydrophobic, non-ionic organic co-solvent to the quaternary phosphonium carboxylate extracting phase.

Thus, in a third aspect, the present invention provides a solvent for extracting lower carboxylic acids ($C_1$-$C_4$) from water. The extraction solvent comprises the phosphonium carboxylate defined by the general formula 1 above and a non-ionic organic (NIO) solvent. The NIO solvent is not the extract (i.e., the $C_1$-$C_4$ carboxylic acid to be separated). Rather, it is separate from and in addition to the lower carboxylic acid to be separated.

The extraction solvent may comprise two or more of the carboxylate salts.

The NIO solvent is preferably selected to impart desirable physical properties to the extraction solvent, such as lower viscosity or higher hydrophobicity or to provide low-boiling azeotropes with water as described above and illustrated in, for example, U.S. Pat. Nos. 1,861,841; 1,917,391; 2,028, 800; 3,052,610; 5,662,780; 2,076,184; and 2,204,616, to enable drying of the lower carboxylic acid in a subsequent purification step.

Examples of such hydrophobic NIO solvents include ketones, aromatic hydrocarbons, saturated hydrocarbons, ethers, esters, chlorinated hydrocarbons, nitriles, and higher carboxylic acids.

Fatty alcohols, such as nonanol, are not preferred as these may complicate the separation of the lower acids by forming esters during extraction or subsequent purification. In one embodiment, the NIO solvent excludes fatty alcohols, such as nonanol.

Likewise, care should be exercised when selecting specific compounds from any of the above classes of co-solvent, which, in combination with the lower acids or water, may form azeotropes or may be difficult to separate from the lower acids.

Preferred non-ionic organic solvents form minimum-boiling azeotropes with water, but do not form azeotropes with the lower acid.

In one embodiment, the NIO solvent has 4 to 20 carbon atoms. In another embodiment, the NIO solvent has 4 to 18 carbon atoms. In other embodiments, the NIO solvent has 4 to 16 carbon atoms, 4 to 14 carbon atoms, 4 to 12 carbon atoms, 5 to 20 carbon atoms, 5 to 18 carbon atoms, 5 to 16 carbon atoms, 5 to 14 carbon atoms, or 5 to 12 carbon atoms.

In one particular embodiment, the NIO solvent comprises a higher carboxylic acid. Remarkably, it has been found that as little as 10 mole percent of a higher carboxylic acid in the extraction solvent can significantly enhance the partition coefficient of the lower acids, especially at low concentration in wet acid streams.

As used herein, "higher carboxylic acids" refer to a carboxylic acid having 4 to 20 carbon atoms. In the case where the carboxylic acid to be separated has 4 carbon atoms, the "higher carboxylic acid" contains at least 5 carbon atoms or has a sufficiently different boiling point (e.g., +/−2° C.) from the lower acid to be separated such that the two may be separated from one another by simple distillation.

In one embodiment, the higher carboxylic acid is selected from the group consisting of n-butyric acid, isobutyric acid, n-valeric acid, isovaleric acid, n-hexanoic acid, 2-ethylbutyric acid, heptanoic acid, n-octanoic, 2-ethylhexanoic acids, nonanoic acids, decanoic acids, dodecanoic acids, stearic acid, oleic acid, linolenic acid, and mixed vegetable-derived acids.

In another embodiment, the higher carboxylic acid is selected from the group consisting of n-butyric acid, isobutyric acid, n-valeric acid, isovaleric acid, n-hexanoic acid, 2-ethylbutyric acid, heptanoic acid, n-octanoic acid, and 2-ethylhexanoic acid.

Preferred NIO esters are those containing four to six carbon atoms such as ethyl acetate, n-propyl acetate, n-propyl formate, i-propyl acetate, i-propyl formate, n-butyl acetate, n-butyl formate, i-butyl acetate, i-butyl formate, n-propyl propionate, and i-propyl propionate.

Preferred NIO ketones are those containing five to nine carbon atoms such as 2-pentanone, 3-pentanone, 3-methyl-2-butanone, 2-hexanone, 2-heptanone, cyclohexanone, 4-methyl-2-pentanone, 2,4-dimethyl-3-pentanone, 5-methyl-2-hexanone, 4-heptanone, 2-octanone, 5-nonanone, 2,8-dimethyl-4-heptanone, 3,3,5-trimethyl cyclohexanone, and isophorone.

Preferred NIO ethers are those containing four to eight carbon atoms such as diethyl ether, methyl propyl ether, dipropyl ether, di-isopropyl ether, methyl tert butyl ether, tertiary amyl methyl ether, and ethyl butyl ether.

Preferred NIO aromatic hydrocarbons include toluene, m-xylene, p-xylene, and o-xylene.

Preferred NIO chlorinated hydrocarbons include methylene chloride, chloroform, dichloroethane, ethylene chloride, carbon tetrachloride, and chlorinated derivatives of benzene.

Preferred NIO nitriles include valeronitrile and nitriles that are higher boiling than valeronitrile, such as hexanenitrile and benzonitrile.

In one embodiment, the hydrophobic NIO solvent is selected from the group consisting of methyl isobutyl ketone, toluene, isopropyl acetate, and methyl t-butyl ether.

In another embodiment, the hydrophobic NIO solvent is a fatty carboxylic acid, such as butyric, pentanoic, hexanoic, heptanoic, octanoic, nonanoic acids, and isomeric forms of $C_4$-$C_9$ carboxylic acids.

The extraction solvent according to the invention and compositions containing the same may include two or more of the NIO solvents. Desirable physical properties of the claimed systems may best be achieved by employing mixtures of the hydrophobic solvents.

The extraction solvent of the invention may comprise from 0 to 90, 10 to 90, 20 to 90, 30 to 90, 40 to 90, or 50 to 90 weight percent of the NIO solvent. The extraction solvent may also comprise from 0 to 60, 10 to 60, 20 to 60, 30 to 60, 40 to 60, or 50 to 60 weight percent of the NIO solvent. The balance of the extraction solvent may be composed of the carboxylate salt according to the invention.

The NIO solvent may be combined with the carboxylate salt before introduction into the extraction vessel. Alternatively, the NIO solvent may be introduced separately into the extraction vessel. In one embodiment, the NIO solvent may be introduced as a second solvent feed on the other side of the extraction cascade from the wet acid feed, such as in a fractional extraction mode, wherein the NIO solvent helps to wash any carboxylate from the final raffinate product stream.

The carboxylate or mixture of carboxylates of the present invention may be mixed with one or more of the NIO solvents to form the extraction solvent in any known manner.

In a fourth aspect, the invention provides a composition B:

$$\left[\begin{array}{c}R^1\underset{R^4}{\overset{R^2}{\underset{\oplus}{P}}}R^3\end{array}\right]\left[\begin{array}{c}O\\\underset{O}{\overset{\ominus}{\parallel}}R^5\end{array}\right] \bigg/ \text{hydrophobic non-ionic co-solvent} \bigg/ \text{water} \bigg/ \text{lower acid} \quad B$$

Composition B comprises the carboxylate salt according to formula 1, the NIO solvent, a $C_1$ to $C_4$ carboxylic acid, and water. It is useful for separating the lower carboxylic acid from water and optionally purifying the lower acid.

Composition B may contain more than one of the carboxylate salt, more than one of the NIO solvent, and/or more than one of the lower acid. The carboxylate salt, NIO solvent, and lower acid may be any of those described herein.

In one embodiment, composition B has only two liquid phases.

A feature of composition B is that the $C_1$ to $C_4$ carboxylic acid may be recovered by distillation at atmospheric pressure or lower.

The weight ratio of the extraction solvent (carboxylate and NIO solvent) to wet acid feed in composition B may vary over a wide range. For example, the ratio may range from 0.2 to 10:1 or, more preferably, from 0.3 to 4:1.

In a fifth aspect, the present invention provides a process for separating a $C_1$ to $C_4$ carboxylic acid from water. The process includes the step of contacting a feed mixture comprising a $C_1$ to $C_4$ carboxylic acid and water with an extraction solvent comprising a quaternary phosphonium carboxylate salt according to the invention and a non-ionic organic solvent according to the invention at conditions effective to form (a) an extract mixture comprising the carboxylate salt, the non-ionic organic solvent, and at least a portion of the $C_1$ to $C_4$ carboxylic acid from the feed mixture and (b) a raffinate mixture comprising water and less of the $C_1$ to $C_4$ carboxylic acid compared to the feed mixture.

The extraction of the feed mixture (i.e., the contacting step) can be carried out by any means known in the art to intimately contact two immiscible liquid phases and to separate the resulting phases after the extraction procedure. For example, the extraction can be carried out using columns, centrifuges, mixer-settlers, and miscellaneous devices. Some representative examples of extractors include unagitated columns (e.g., spray, baffle tray and packed, perforated plate), agitated columns (e.g., pulsed, rotary agitated, and reciprocating plate), mixer-settlers (e.g., pump-settler, static mixer-settler, and agitated mixer-settler), centrifugal extractors (e.g., those produced by Robatel, Luwesta, deLaval, Dorr Oliver, Bird, CINC, and Podbielniak), and other miscellaneous extractors (e.g., emulsion phase contactor, electrically enhanced extractors, and membrane extractors). A description of these devices can be found in the "Handbook of Solvent Extraction," Krieger Publishing Company, Malabar, F L, pp. 275-501 (1991). The various types of extractors may be used alone or in any combination.

The extraction may be conducted in one or more stages. The number of extraction stages can be selected based on a number of factors, such as capital costs, achieving high extraction efficiency, ease of operability, the stability of the feed and the extraction solvent, and the extraction conditions. The extraction also can be conducted in a batch or continuous mode of operation. In a continuous mode, the extraction may be carried out in a co-current, a counter-current manner, or as a fractional extraction in which multiple solvents and/or solvent feed points are used to help facilitate the separation. The extraction process also can be conducted in a plurality of separation zones that can be in series or in parallel.

The extraction may be carried out at an extraction solvent: feed mixture weight ratio of, for example, 0.2 to 10:1 or, more preferably, 0.3 to 4:1.

The extraction typically can be carried out at a temperature of 10 to 140° C. For example, the extraction can be conducted at a temperature of 30 to 110° C. The desired temperature range may be constrained further by the boiling point of the extractant components or water. Generally, it is undesirable to operate the extraction under conditions where the extractant boils. In one embodiment, the extractor can be operated to establish a temperature gradient across the extractor in order to improve the mass transfer kinetics or decantation rates.

If the temperature chosen for the extraction is greater than the normal boiling point of any of the lower acid to be extracted, any of the components comprising the extraction solvent, or water; then the extractor may be run under sufficient pressure to suppress boiling of any of aforementioned components. The extraction typically can be carried out at a pressure of 1 bara to 10 bara, or 1 bara to 5 bara.

The separation process according to the invention may further include the steps of separating the extract from the raffinate and recovering the $C_1$ to $C_4$ carboxylic acid from the extract by distillation at atmospheric pressure or lower. Any known method from separating a liquid extract from a raffinate may be used. Likewise, any known distillation technique may be used to recover the lower acid from the extraction solvent.

In one embodiment, the present invention provides a process for separating acetic acid from water. The process comprises contacting a feed mixture comprising acetic acid and water with an extraction solvent comprising a quaternary phosphonium carboxylate salt according to the invention at conditions effective to form (a) an extract mixture comprising the carboxylate salt and at least a portion of the acetic acid from the feed mixture and (b) a raffinate mixture comprising water and less of the acetic acid compared to the feed mixture.

This acetic acid separation process may be carried out using any of the modes described herein above.

The extraction solvent used in this process may further comprise one or more of the NIO solvents according to the invention.

The acetic acid separation process may further include the steps of separating the extract mixture from the raffinate mixture and recovering the acetic acid from the extract mixture by distillation at atmospheric pressure or lower.

These additional steps may also be carried out as described herein above.

The present invention includes and expressly contemplates any and all combinations of embodiments, features, and/or ranges disclosed herein. That is, the invention may be defined by any combination of embodiments, features, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Abbreviations used in the following examples are summarized in Table 2.

TABLE 2

Abbreviations

| Compound | Abbreviation |
|---|---|
| acetic acid | HOAc |
| propionic acid | HOPr |
| n-butyric acid | n-HOBu |
| isobutyric acid | i-HOBu |
| 2,2-dimethylbutyric acid | 2,2-DMB acid |
| 2-ethylbutyric acid | 2EB acid |
| 2-ethylhexanoic acid | 2EH acid |
| butyronitrile | PrCN |
| methyl t-butyl ether | MTBE |
| t-amyl methyl ether | TAME |
| 4-heptanone | DPK |
| ethyl acetate | EtOAc |
| i-propyl acetate | i-PrOAc |
| n-propyl acetate | n-PrOAc |
| n-butyl acetate | n-BuOAc |
| i-butyl acetate | i-BuOAc |
| 2-pentanone | MPK |
| 4-methyl-2-pentanone | MIBK |
| 5-methyl-2-hexanone | MIAK |
| 2-heptanone | MAK |
| tributyl phosphate | TBP |
| triethylhexyl phosphate | TEHP |
| Cyanex 923: a mixture of trialkyl phosphine oxides with octyl and hexyl groups | C923 |
| 1-ethyl-3-methyl imidazolium bis(trifluoromethylsulfonyl)imide | emim-NTf$_2$ |
| 1-butyl-3-methyl imidazolium bis(trifluoromethylsulfonyl)imide | bmim-NTf$_2$ |
| 1-butyl-3-methyl imidazolium acetate | bmim-OAc |
| 1-butyl-3-methyl imidazolium bis(trifluoroethylsulfonyl)imide | bmim-BETI |
| 1-butyl-3-methyl imidazolium tris(pentafluoroethyl)trifluorophosphate | bmim-FAP |
| 1-hexyl-3-methyl imidazolium bis(trifluoromethylsulfonyl)imide | hmim-NTf$_2$ |
| 1-octyl-3-methyl imidazolium bis(trifluoromethylsulfonyl)imide | omim-NTf$_2$ |
| 1-octyl-3-methyl imidazolium bis(trifluoromethylsulfonyl)imide | omim-BETI |
| 1-decyl-3-methyl imidazolium bis(trifluoromethylsulfonyl)imide | C$_{10}$mim-NTf$_2$ |
| 1-butyl-2,3-dimethyl imidazolium bis(trifluoromethylsulfonyl)imide | C$_4$mmim-NTf$_2$ |
| 1-(2-methoxyethyl)-3-methyl imidazolium tris(pentafluoroethyl)trifluorophosphate | MeOEtmim-FAP |
| 1-(8-hydroxyoctyl)-3-methylimidazolium bis(trifluoromethylsulfonyl)imide | HOC$_8$mim-NTf$_2$ |
| tridecafluoro-octyl)-3-methylimidazolium bis(trifluoromethylsulfonyl)imide | C$_8$—H$_4$F$_{13}$mim-NTf$_2$ |
| dimethylaminoethyl-dimethylethylammonium bis(trifluoromethyl)sulfonylimide | iPr$_2$N(CH$_2$)$_2$mim-NTf$_2$ |
| 1-butyl pyridinium bis(trifluoromethylsulfonyl)imide | bpyr-NTf$_2$ |
| 1-(2-methoxyethyl)-pyridinium tris(pentafluoroethyl)trifluorophosphate | MeOEtpyr-FAP |
| 1-(4-cyanobutyl)-3-methyl imidazolium bis(trifluoromethylsulfonyl)imide | (4-CN)bmim-NTf$_2$ |
| trimethyl(butyl)ammonium bis(trifluoromethylsulfonyl)imide | N$_{1114}$-NTf$_2$ |

TABLE 2-continued

Abbreviations

| Compound | Abbreviation |
|---|---|
| trimethyl(octyl)ammonium bis(trifluoromethylsulfonyl)imide | N$_{1118}$-NTf$_2$ |
| 1-(2-diisopropylaminoethyl) dimethylethyl-ammonium bis(trifluoromethyl)sulfonylimide | iPr$_2$N(CH$_2$)$_2$N$_{211}$-NTf$_2$ |
| dimethylaminoethyl-dimethylethylammonium bis(trifluoromethyl)sulfonylimide | Me$_2$N(CH$_2$)$_2$N$_{211}$-NTf$_2$ |
| choline bis(trifluoromethylsulfonyl)imide | choline-NTf$_2$ |
| 1-butyl-1-methyl pyrrolidinium bis(trifluoromethylsulfonyl)imide | C4mpyrr-NTf$_2$ |
| N-trimethylbetainium bis(trifluoromethylsulfonyl)imide | C$_1$Hbet-NTf$_2$ |
| triethyl(octyl)phosphonium bis(trifluoromethylsulfonyl)imide | P$_{2228}$-NTf$_2$ |
| trioctyl(methyl)phosphonium bis(trifluoromethylsulfonyl)imide | P$_{8881}$-NTf$_2$ |
| 1-(2-diisopropylaminoethyl) trioctyl-phosphonium bis(trifluoromethyl)sulfonylimide | iPr$_2$N(CH$_2$)$_2$P$_{888}$-NTf$_2$ |
| trihexyl(tetradecyl)phosphonium chloride | P$_{666,14}$-Cl |
| trihexyl(tetradecyl)phosphonium hydroxide | P$_{666,14}$-OH |
| trihexyl(tetradecyl)phosphonium bis(trifluoromethylsulfonyl)imide | P$_{666,14}$-NTf2 |
| trihexyl(tetradecyl)phosphonium tris(pentafluoroethyl)trifluorophosphate | P$_{666,14}$-FAP |
| trihexyl(tetradecyl)phosphonium formate | P$_{666,14}$-formate |
| trihexyl(tetradecyl)phosphonium acetate | P$_{666,14}$-OAc |
| trihexyl(tetradecyl)phosphonium isobutyrate | P$_{666,14}$-isobutyrate |
| trihexyl(tetradecyl)phosphonium hexanoate | P$_{666,14}$-hexanoate |
| trihexyl(tetradecyl)phosphonium 2-ethylbutyrate | P$_{666,14}$-2EB |
| trihexyl(tetradecyl)phosphonium 2,2-dimethylbutyrate | P$_{666,14}$-2,2-DMB |
| trihexyl(tetradecyl)phosphonium octanoate | P$_{666,14}$-octanoate |
| trihexyl(tetradecyl)phosphonium 2-ethylhexanoate | P$_{666,14}$-2EH |
| trihexyl(tetradecyl)phosphonium dodecanoate | P$_{666,14}$-dodecanoate |
| trihexyl(tetradecyl)phosphonium succinate | P$_{666,14}$-succinate |

Example 1

Synthesis of P$_{666,14}$-OH

P$_{666,14}$-Cl (81.70 g, 157.32 mmol) was dissolved in methanol (19.78 g, 617.35 mmol), and the solution was settled for further ion-exchange reaction. A column was packed with ion exchange resin (170 cm$^3$, Amberlite IRN-78), and the resin was washed with methanol. The P$_{666,14}$-Cl solution was then added slowly to the column, with the flow rate controlled at 1 droplet/2 s. Thereafter, methanol (80 mL, 1977.03 mmol) was added slowly into the column to wash out all the P$_{666,14}$-OH into a 500 mL single-neck round bottom flask. After all the solution containing P$_{666,14}$-OH in the column was collected, 5 droplets from the solution were mixed with 3 droplets of HNO$_3$ and 3 droplets of AgNO$_3$ to test if all of the halide had been exchanged. Where necessary, this procedure was repeated.

The concentration of P$_{666,14}$-OH in solution was analyzed by $^1$H NMR, and a wt % of P$_{666,14}$-OH in methanol was determined by the relative integrations of the acidic protons versus the methyl group of methanol versus the hydrocarbon chains of the phosphonium salt.

Example 2

Synthesis of $P_{666,14}$-2EH

From the calculated weight fraction of $P_{666,14}$-OH in methanol determined in Example 1 (weight fraction of $P_{666,14}$-OH=0.3032), the acid needed to neutralize the $P_{666,14}$-OH was calculated as follows:

MW of 2-EH Acid=144.21;
MW of $P_{666,14}$-OH=500.86;

weight of 2-EH Acid needed={[(weight of hydroxide MeOH solution)*(wt % of $P_{666,14}$-OH)]/(MW of $P_{666,14}$-OH)}*(MW of 2-EH Acid)={[(252.36 g)*[0.3032/(500.86 g/mol)]}*(144.12 g/mol)=22.017 g.

2-Ethylhexanoic acid (22.04 g, 152.93 mmol) was added into the $P_{666,14}$-OH solution, and the solution was then stirred for 6 h. The solution was then dried in a rotary evaporator at 40° C. for 6 h. Further drying was conducted in a high vacuum drying system for 6 h. The formed carboxylate was then ready for liquid-liquid extraction (LLE) experimentation and further characterization, such as water content measurement, differential scanning calorimetry, thermogravimetric analysis, and elemental analysis.

The $^1$H NMR Spectrum of pure $P_{666,14}$-2EH in CDCl$_3$ at 300 MHz is shown in the FIGURE.

Example 3

Extraction of Acetic Acid Using Representative NIO Solvents

Tie line data at both high (typically around 16-20 wt % of HOAc in the organic phase) and low acetic acid concentrations (typically around 1 to 5 wt % of HOAc in the organic phase) were measured for each solvent at the temperature given in Table 3.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 3.

TABLE 3

Acetic Acid Extraction Factors of Non-Ionic Organic Solvents

| Solvent | T (° C.) | $P_{cont}$ | HOAc at $P_{cont}$ (wt %) | $R_{extr}$ | Extraction Factor ($\epsilon$) |
|---|---|---|---|---|---|
| EtOAc | 25 | 0.99 | 1.5 | 0.98 | 1.01 |
| n-BuOAc | 40 | 0.41 | 1.6 | 0.52 | 0.79 |
| nPrOAc | 40 | 0.51 | 2.2 | 0.70 | 0.73 |
| iPrOAc | 40 | 0.54 | 1.8 | 0.65 | 0.83 |
| PrCN | 20 | 2.85 | 17.0 | 0.7 | 4.07 |
| 2EH Acid | 40 | 0.32 | 1.3 | 0.29 | 1.10 |
| MTBE | 40 | 0.7 | 2.0 | 0.5 | 1.40 |
| TAME | 40 | 0.42 | 1.5 | 0.34 | 1.24 |
| 2-hexanone[a] | 35 | 0.91 | 3.9 | 0.97 | 0.93 |
| MIBK | 35 | 0.65 | 1.6 | 0.53 | 1.23 |
| MAK | 40 | 0.49 | 1.7 | 0.41 | 1.20 |
| MIAK | 40 | 0.46 | 1.7 | 0.34 | 1.35 |
| DPK | 40 | 0.32 | 1.3 | 0.31 | 1.03 |
| isophorone | 40 | 1.1 | 1.2 | 0.67 | 1.64 |

[a]Data taken from *J. Chem. Eng. Data*, 46, 2001, 1450-56.

Although PrCN has a relatively high extraction factor, it has the same boiling point as acetic acid, forms an azeotrope with acetic acid, and is thus very difficult to separate from acetic acid.

Example 4

Extraction of Acetic Acid Using Phosphate Ester Solvents

Tie line data at both high (typically around 15-20 wt % of HOAc in the organic phase) and low acetic acid concentrations (typically around 1 to 2 wt % of HOAc in the organic phase) were measured for each solvent (either a pure phosphate ester or a mixture of phosphate ester with a NIO solvent) at the temperature given in Table 4.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 4.

TABLE 4

Acetic Acid Extraction by Phosphate-Ester-Containing Compositions at 40° C.

| Solvent | $P_{cont}$ | HOAc at $P_{cont}$ (wt %) | $R_{extr}$ | Extraction Factor ($\epsilon$) |
|---|---|---|---|---|
| tributyl phosphate | 0.78 | 18.1 | 0.39 | 2.00 |
| 25 wt % TBP, 75 wt % MTBE | 0.94 | 19.7 | 0.52 | 1.81 |
| 25 wt % TBP, 75 wt % iPrOAc | 0.80 | 18.1 | 0.61 | 1.31 |
| triethylhexyl phosphate | 0.33 | 16.2 | 0.12 | 2.75 |
| 25 wt % TEHP, 75 wt % MTBE | 0.71 | 16.9 | 0.30 | 2.37 |
| 25 wt % TEHP, 75 wt % iPrOAc | 0.62 | 15.8 | 0.39 | 1.59 |

As expected from Wardell and King ("Solvent Equilibria for Extraction of Carboxylic Acids from Water," *J. Chem. and Eng. Data*, Vol. 23, No. 2, pp. 144-148 (1978)), the extraction factors for phosphate ester solvents are somewhat improved over those of NIO solvents.

Example 5

Extraction of Acetic Acid Using Cyanex 923

Tie line data at both high (typically around 15-20 wt % of HOAc in the organic phase) and low acetic acid concentrations (typically around 1 to 2 wt % of HOAc in the organic phase) were measured for each solvent (either commercially available Cyanex 923 or a mixture of Cyanex 923 with a non-ionic organic solvent) at the temperature given in Table 5.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 5.

TABLE 5

Acetic Acid Extraction Factors for Cyanex-Containing Compositions at 40° C.

| Solvent | $P_{cont}$ | HOAc at $P_{cont}$ (wt %) | $R_{extr}$ | Extraction Factor ($\epsilon$) |
|---|---|---|---|---|
| Cyanex 923 | 0.94 | 19.0 | 0.26 | 3.62 |
| 75 wt % MTBE/25 wt % C923 | 0.89 | 20.0 | 0.36 | 2.47 |
| 75 wt % iPrOAc/25 wt % C923 | 0.77 | 20.0 | 0.43 | 1.79 |

Example 6

Extraction of Acetic Acid Using Hydrophobic Liquid Salts

Tie line data at both high (typically around 7-25 wt % of HOAc in the organic phase) and low acetic acid concentrations (typically around 0.2 to 5 wt % of HOAc in the organic phase) were measured for each solvent at the temperature specified in Table 6.

Some solvents showed extremely low acid partition coefficients, and the two-phase region did not extend much above about 7 wt % of acetic acid. Equilibrium data were measured for each compound in the following manner.

Three grams of the solvent were pipetted into a jacketed glass cell, wherein three grams of an aqueous mixture of acetic acid (prepared to yield either high or low acid concentration data) were added. A stir bar was introduced to the vial and the contents sealed with a plastic cap and a layer of parafilm tape. The cell was maintained at the desired temperature by means of a thermostatted fluid circulating through the cell jacket. The mixture was agitated vigorously for 1.5 hours and then allowed to separate into clear phases while maintaining the specified temperature without stirring. After a six hour settling time, each phase was sampled and analyzed by NMR for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 6.

TABLE 6

Extraction of Acetic Acid in a Selection of Hydrophobic Solvents at 20° C.

| Solvent | $P_{cont}$ | HOAc at $P_{cont}$ (wt %) | $R_{extr}$ | Extraction Factor ($\epsilon$) |
|---|---|---|---|---|
| emim-NTf$_2$ | 0.30 | 7.1 | 0.85 | 0.35 |
| bmim-NTf$_2$ | 0.21 | 1.4 | 0.69 | 0.31 |
| bmim-NTf$_2$[b] | 0.24 | 5.4 | 0.79 | 0.30 |
| bmim-FAP | 0.00 | 1.5 | 0.17 | 0.00 |
| bmim-FAP[b] | 0.06 | 1.7 | 0.33 | 0.18 |
| bmim-BETI | 0.06 | 0.6 | 0.39 | 0.15 |
| hmim-NTf$_2$ | 0.19 | 4.6 | 0.56 | 0.34 |
| omim-NTf$_2$ | 0.18 | 0.9 | 0.47 | 0.38 |
| omim-NTf$_2$[a] | 0.12 | 11.8 | 0.68 | 0.17 |
| omim-BETI | 0.05 | 0.5 | 0.50 | 0.11 |
| C$_{10}$mim-NTf$_2$ | 0.13 | 3.6 | 0.39 | 0.34 |
| C$_4$mim-NTf$_2$ | 0.13 | 1.1 | 0.59 | 0.22 |
| iPr$_2$N(CH$_2$)$_2$mim-NTf$_2$ | 0.18 | 4.5 | 0.88 | 0.20 |
| MeOEtmim-FAP | 0.04 | 0.3 | 0.23 | 0.15 |
| 4CNbmim-NTf$_2$ | 0.65 | 11.0 | 0.82 | 0.79 |
| HOC$_8$mim-NTf$_2$ | 0.54 | 7.6 | 0.98 | 0.55 |
| (C$_6$F$_{13}$)—(C$_2$H$_4$)mim-NTf$_2$ | 0.08 | 0.7 | 0.60 | 0.13 |
| C$_4$mpyrr-NTf$_2$ | 0.33 | 9.5 | 0.45 | 0.74 |
| bpyr-NTf$_2$ | 0.22 | 5.1 | 0.69 | 0.31 |
| MeOEtpyr-FAP | 0.06 | 0.2 | 0.23 | 0.26 |
| N$_{1114}$-NTf$_2$ | 0.13 | 1.9 | 0.84 | 0.16 |
| N$_{1118}$-NTf$_2$ | 0.06 | 1.2 | 0.47 | 0.14 |
| Me$_2$N(CH$_2$)$_2$N$_{211}$-NTf$_2$ | 0.53 | 9.5 | 2.00 | 0.26 |
| iPr$_2$N(CH$_2$)$_2$N$_{211}$-NTf$_2$ | 0.14 | 4.0 | 0.77 | 0.19 |
| choline-NTf$_2$ | 0.82 | 14.0 | 1.64 | 0.50 |
| C$_1$Hbet-NTf$_2$ | 0.76 | 12.7 | 1.48 | 0.51 |
| P$_{2228}$-NTf$_2$[b] | 0.10 | 2.8 | 0.33 | 0.30 |
| P$_{4444}$-2EH | 0.52 | 7.3 | 1.452 | 0.36 |
| P$_{8881}$-NTf$_2$ | 0.05 | 0.8 | 0.43 | 0.13 |
| iPr$_2$N(CH$_2$)$_2$P$_{888}$-NTf$_2$ | 0.21 | 5.4 | 0.74 | 0.28 |
| P$_{666,14}$-Cl | 0.38 | 8.5 | 0.63 | 0.60 |
| P$_{666,14}$-NTf$_2$ | 0.06 | 1.8 | 0.88 | 0.07 |
| P$_{666,14}$-FAP | 0.02 | 0.1 | 0.23 | 0.10 |

[a]Equilibration at 75° C. rather than 20° C.
[b]Data taken from Hashikawa, JP Appl. Kokai 2014/40389.

Example 7

Extraction of Acetic Acid Using Tetraalkylphosphonium Carboxylates

Tie line data at both high (typically around 9-21 wt % of HOAc in the organic phase) and low acetic acid concentrations (typically around 0.2 to 5 wt % of HOAc in the organic phase) were measured at 20° C. for each solvent listed in Table 7.

Roughly equal masses of water and solvent were added to a glass vial. All extraction solvents comprised essentially 100 mole percent of the carboxylate. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by NMR for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 7.

TABLE 7

Acetic Acid Extraction by Different Phosphonium Carboxylates at 20° C.

| Solvent | $P_{cont}$ | HOAc at $P_{cont}$ (wt %) | $R_{extr}$ | Extraction Factor ($\epsilon$) |
|---|---|---|---|---|
| $P_{666,14}$-formate | 2.47 | 19.7 | 0.28 | 8.73 |
| $P_{666,14}$-acetate | 4.98 | 9.1 | 1.08 | 4.59 |
| $P_{666,14}$-hexanoate | 3.32 | 20.3 | 0.25 | 13.48 |
| $P_{666,14}$-2EB | 2.15 | 21.6 | 0.24 | 8.91 |
| $P_{666,14}$-2,2-DMB | 2.41 | 20.3 | 0.29 | 8.32 |
| $P_{666,14}$-octanoate | 3.17 | 19.9 | 0.24 | 12.99 |
| $P_{666,14}$-2EH | 3.24 | 20.4 | 0.21 | 15.21 |
| $P_{666,14}$-dodeconoate | 2.62 | 20.2 | 0.23 | 11.17 |
| $P_{666,14}$-succinate | 4.72 | 11.9 | 0.58 | 8.07 |

Example 8

Extraction of $C_1$ to $C_4$ Carboxylic Acids Using $P_{666,14}$-2EH

Tie line data at both high (typically around 16-25 weight percent of lower acid in the organic phase) and low acid concentrations (typically around 0.2 to 5 weight percent in the organic phase) were measured at 20° C. for each acid listed in Table 8.

Roughly equal masses of water and solvent were added to a glass vial. All extraction solvents comprised essentially 100 mole percent of the carboxylate. The acid was added to the solvent-water mixture in amounts sufficient to yield either high or low acid concentration data. Once the lower acid was added, the mixture was agitated vigorously, and subsequently was allowed to separate into clear phases while maintaining the specified temperature. Each phase was sampled and analyzed by NMR for water and lower acid weight percent. These data were used to calculate partition coefficients, with the controlling partition coefficient, $P_{cont}$, taken as the lesser of the partition coefficients at high and low acid concentrations. The data were also used to calculate the water to acid weight ratio at high acid concentration, $R_{extr}$. Results are given in Table 8.

TABLE 8

Extraction of a Variety of Carboxylic Acids by $P_{666,14}$-2EH

| Solute Acid | $P_{cont}$ | Carboxylic Acid at $P_{cont}$ (wt %) | $R_{extr}$ | Extraction Factor ($\epsilon$) |
|---|---|---|---|---|
| formic | 1.35 | 16.5 | 0.19 | 7.03 |
| acetic | 3.24 | 20.4 | 0.21 | 15.21 |
| propionic | 7.64 | 25.1 | 0.16 | 47.28 |
| n-butyric | 4.64 | 22.0 | 0.17 | 27.05 |
| acrylic | 4.77 | 20.9 | 0.16 | 28.49 |

Example 9

Extraction of Acetic Acid Using $P_{666,14}$-2EH and/or NIO Co-Solvent

Tie line data at both high (typically around 20 to 25 wt % of HOAc in the organic phase) and low acetic acid concentrations (typically around 0.2 to 5 wt % of HOAc in the organic phase) were measured at 20° C. for each solvent listed in Table 9.

Roughly equal masses of water and extraction solvent comprising different amounts of the carboxylate and the NIO solvents were added to a glass vial. Both n-hexanoic acid and 2-ethylhexanoic acid (2-EH acid) were tested as the NIO solvent. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by NMR for water and acetic acid (wt %). These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 9.

Extraction results with 2-EH acid alone and n-hexanoic acid alone are included in Table 9 for comparison.

TABLE 9

Effect of NIO Solvent Identity and Concentration on Acetic Acid Extraction

| Carboxylate Solvent | NIO Solvent | $P_{cont}$ | HOAc at $P_{cont}$ (wt %) | $R_{extr}$ | Extraction Factor ($\epsilon$) |
|---|---|---|---|---|---|
| none | 100 mol % 2-EH acid[a] | 0.32 | 0.32 | 0.29 | 1.10 |
| none | 100 mol % n-hexanoic acid | 0.56 | 1.8 | 1.07 | 0.53 |
| $P_{666,14}$-2EH | none | 3.24 | 20.4 | 0.21 | 15.21 |
| $P_{666,14}$-2EH | 10 mol % 2-EH acid | 2.19 | 21.7 | 0.21 | 10.40 |
| $P_{666,14}$-2EH | 30 mol % 2-EH acid | 1.80 | 19.7 | 0.22 | 8.18 |
| $P_{666,14}$-2EH | 50 mol % 2-EH acid | 0.86 | 23.9 | 0.22 | 3.87 |
| $P_{666,14}$-2EH | 80 mol % 2-EH acid | 0.53 | 25.8 | 0.30 | 1.79 |
| $P_{666,14}$-2EH | 90 mol % 2-EH acid | 0.48 | 25.0 | 0.46 | 1.05 |
| $P_{666,14}$-2EH | 10 mol % n-hexanic acid | 2.26 | 20.9 | 0.22 | 10.03 |
| $P_{666,14}$-2EH | 20 mol % n-hexanoic acid | 1.97 | 20.5 | 0.22 | 8.73 |
| $P_{666,14}$-2EH | 30 mol % n-hexanoic acid | 2.00 | 19.6 | 0.24 | 8.31 |
| $P_{666,14}$-2EH | 50 mol % n-hexanoic acid | 1.15 | 20.5 | 0.27 | 4.21 |

[a]Equilibrated at 40° C.

Example 10

Extraction of Acetic Acid Using $P_{666,14}$-n-Hexanoate and/or n-Hexanoic Acid Tie line data at both high (typically around 20 wt % of HOAc in the organic phase) and low acetic acid concentrations (typically around 0.2 to 5 wt % of HOAc in the organic phase) were measured at 20° C. for each solvent listed in Table 10.

Roughly equal masses of water and extraction solvent comprising different amounts of carboxylate and NIO solvent were added to a glass vial. N-hexanoic acid was tested as the NIO solvent. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by NMR for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 10.

Extraction results with n-hexanoic acid alone are included in Table 10 for comparison.

TABLE 10

Effect of n-Hexanoic Acid on Acetic Acid Extraction by $P_{666,14}$-Hexanoate

| Amount of n-Hexanoic Acid (mole %) | $P_{cont}$ | HOAc at $P_{cont}$ (wt %) | $R_{extr}$ | Extraction Factor ($\epsilon$) |
|---|---|---|---|---|
| none | 3.32 | 20.3 | 0.25 | 13.48 |
| 30 | 2.97 | 19.3 | 0.26 | 11.36 |
| 50 | 1.80 | 19.6 | 0.27 | 6.63 |
| 70 | 1.15 | 15.4 | 0.43 | 2.69 |
| 90 | 0.65 | 14.7 | 0.86 | 0.76 |
| 95 | 0.68 | 14.3 | 1.19 | 0.57 |
| 100 | 0.56 | 1.8 | 1.07 | 0.53 |

Example 11

Extraction of Acetic Acid Using $P_{666,14}$-2EB and/or 2-EB Acid

Tie line data at both high (typically around 14 to 20 wt % of HOAc in the organic phase) and low acetic acid concentrations (typically around 0.2 to 5 wt % of HOAc in the organic phase) were measured at 20° C. for each solvent listed in Table 11.

Roughly equal masses of water and extraction solvent comprising different amounts of the carboxylate and NIO solvent were added to a glass vial. 2-Ethylbutyric acid was tested as the NIO solvent. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by NMR for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 11.

TABLE 11

Effect of 2-EB acid on Acetic Acid Extraction by $P_{666,14}$-2EB

| Amount of 2-EB Acid (mole %) | $P_{cont}$ | HOAc at $P_{cont}$ (wt %) | $R_{extr}$ | Extraction Factor ($\epsilon$) |
|---|---|---|---|---|
| none | 2.15 | 21.6 | 0.24 | 8.91 |
| 10 | 4.75 | 20.7 | 0.24 | 19.80 |
| 30 | 2.76 | 22.6 | 0.26 | 10.58 |
| 50 | 2.05 | 19.9 | 0.29 | 7.05 |
| 70 | 1.59 | 14.4 | 0.50 | 3.18 |
| 80 | 1.01 | 14.4 | 0.63 | 1.61 |
| 90 | 1.01 | 14.2 | 0.85 | 1.19 |
| 95 | 0.82 | 14.2 | 1.10 | 0.74 |

Example 12

Extraction of Acetic Acid Using $P_{666,14}$-Isobutyrate and i-HOBu

Tie line data at both high (typically around 20 wt % of HOAc in the organic phase) and low acetic acid concentrations (typically around 0.2 to 5 wt % of HOAc in the organic phase) were measured at 20° C. for each solvent listed in Table 12.

Roughly equal masses of water and extraction solvent comprising different amounts of the carboxylate and NIO solvent were added to a glass vial. Isobutyric acid was tested as the NIO solvent. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by NMR for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 12.

TABLE 12

Effect of Isobutyric Acid on Acetic Acid Extraction by $P_{666,14}$-Isobutyrate

| Amount of Isobutyric Acid (mole %) | $P_{cont}$ | HOAc at $P_{cont}$ (wt %) | $R_{extr}$ | Extraction Factor ($\epsilon$) |
|---|---|---|---|---|
| 10 | 3.19 | 19.3 | 0.273 | 11.69 |
| 30 | 2.08 | 20.6 | 0.255 | 8.16 |
| 50 | 1.67 | 18.8 | 0.275 | 6.08 |

Example 13

Extraction of Acetic Acid Using $P_{666,14}$-n-Octanoate and/or N-Octanoic Acid

Tie line data at both high (typically around 20 to 25 wt % of HOAc in the organic phase) and low acetic acid concentrations (typically around 0.2 to 5 wt % of HOAc in the organic phase) were measured at 20° C. for each solvent listed in Table 13.

Roughly equal masses of water and extraction solvent comprising different amounts of the carboxylate and NIO solvent were added to a glass vial. N-octanoic acid was tested as the NIO solvent. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by NMR for water and acetic acid weight percent. These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$. Results are given in Table 13.

TABLE 13

Effect of Octanoic Acid on Acetic Acid Extraction by $P_{666,14}$-Octanoate

| Amount of Octanoic Acid (mole %) | $P_{cont}$ | HOAc at $P_{cont}$ (wt %) | $R_{extr}$ | Extraction Factor ($\epsilon$) |
|---|---|---|---|---|
| none | 3.17 | 19.9 | 0.24 | 12.99 |
| 50 | 1.03 | 25.7 | 0.21 | 4.76 |

Example 14

Effect of Temperature on Extraction of Acetic Acid Using NIO Solvents

Tie line data were measured at 22 and 40° C. for each solvent listed in Table 14.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent. These data were used to calculate partition coefficients, with the controlling partition coefficient, $P_{cont}$, taken as the lesser of the partition coefficients at high and low acid concentrations. Results are given in Table 14.

TABLE 14

The Effect of Temperature on Acetic Acid Partitioning in NIO Solvents

| Solvent | T (° C.) | $P_{cont}$ | HOAc at $P_{cont}$ (wt %) | $R_{extr}$ | Extraction Factor ($\epsilon$) |
|---|---|---|---|---|---|
| MTBE | 22 | 0.86 | 2.0 | 0.46 | 1.88 |
| MTBE | 40 | 0.70 | 2.0 | 0.50 | 1.40 |
| MIBK | 22 | 0.67 | 3.9 | 1.14 | 0.59 |
| MIBK | 40 | 0.75 | 8.4 | 0.73 | 1.02 |
| i-PrOAc | 22 | 0.57 | 1.7 | 0.56 | 1.02 |
| i-PrOAc | 40 | 0.54 | 1.8 | 0.65 | 0.83 |

As seen from Table 14, the partition coefficient and extraction factor responds in different ways to changes in temperature in different NIO solvents.

Example 15

Effect of Temperature on Extraction of Acetic Acid Using $P_{666,14}$-Carboxylates Tie line data were measured at 20 and 75° C. for each solvent listed in Table 15.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent. These data were used to calculate partition coefficients, with the controlling partition coefficient, $P_{cont}$, taken as the lesser of the partition coefficients at high and low acid concentrations. Results are given in Table 15.

TABLE 15

Effect of Temperature on Extraction of Acetic Acid by $P_{666,14}$-Carboxlates

| Carboxylate Solvent | NIO Solvent | T (° C.) | $P_{cont}$ | HOAc at $P_{cont}$ (wt %) | $R_{extr}$ | Extraction Factor ($\epsilon$) |
|---|---|---|---|---|---|---|
| $P_{666,14}$-2EH | none | 20 | 3.24 | 20.4 | 0.21 | 15.21 |
| $P_{666,14}$-2EH | none | 75 | 1.86 | 20.2 | 0.24 | 7.59 |
| $P_{666,14}$-hexanoate | none | 20 | 3.32 | 20.3 | 0.25 | 13.48 |
| $P_{666,14}$-hexanoate | none | 75 | 1.89 | 21.0 | 0.12 | 16.15 |
| $P_{666,14}$-hexanoate | 10 mol % hexanoic acid | 75 | 2.14 | 21.5 | 0.24 | 8.91 |
| $P_{666,14}$-2EB | none | 20 | 2.15 | 21.6 | 0.24 | 8.91 |
| $P_{666,14}$-2EB | none | 75 | 1.87 | 20.9 | 0.27 | 6.94 |
| $P_{666,14}$-2EB | 10 mol % 2-EB acid | 75 | 2.24 | 20.0 | 0.26 | 8.63 |

As with NIO solvents (see Table 14), the partition coefficients and extraction factors both increase and decrease with respect to temperature in different phosphonium carboxylate solvents (see Table 15). It is notable that, in some cases, the extraction factor increases with increasing temperature.

Procedure for Examples 16 Through 19

Tie line data were measured for the extraction of lower carboxylic acids (formic acid, propionic acid, n-butyric acid, and acrylic acid) from water using three NIO solvents MIBK, MTBE, and n-butyl acetate, and a carboxylate solvent $P_{666,14}$-2EH.

Tie line data at both high (typically around 10-25 wt % of carboxylic acid in the organic phase) and low acid concentrations (typically around 1 to 5 wt % of acid in the organic phase) were measured for each solvent at 40° C.

Roughly equal masses of water and solvent were added to a glass vial. The desired amount of carboxylic acid was added to the solvent-water mixture in amounts sufficient to yield either high or low acid concentration data. Once the acid was added, the mixture was agitated vigorously, and subsequently was allowed to separate into clear phases while maintaining the specified temperature. Each phase was sampled and analyzed by gas chromatography for water and carboxylic acid weight percent. These data were used to calculate partition coefficients, with the controlling partition coefficient, $P_{cont}$, taken as the lesser of the partition coefficients at high and low acid concentrations. The data were also used to calculate the water to carboxylic acid weight ratio at high acid concentration, $R_{extr}$.

Example 16

Extraction of Formic Acid with NIO Solvents Compared to $P_{666,14}$-2EH

This example presents extraction factors for the extraction of formic acid with NIO solvents MTBE, MIBK, and n-butyl acetate, and $P_{666,14}$-2EH following the extraction procedure outlined above. Results are presented in Table 16.

TABLE 16

Partitioning of Formic Acid in NIO Solvents and $P_{666,14}$-2EH (40° C.)

| Solvent | $P_{cont}$ | HOAc at $P_{cont}$ (wt %) | $R_{extr}$ | Extraction Factor (ε) |
|---|---|---|---|---|
| MTBE | 0.7 | 16.8 | 0.69 | 1.0 |
| MIBK | 0.6 | 14.3 | 0.74 | 0.8 |
| BuOAc | 0.4 | 10.0 | 0.58 | 0.6 |
| $P_{666,14}$-2EH | 1.35 | 16.5 | 0.191 | 7.0 |

Example 17

Extraction of Propionic Acid with NIO Solvents Compared to $P_{666,14}$-2EH

This example presents extraction factors for the extraction of propionic acid with NIO solvents MTBE, MIBK, and n-butyl acetate, and $P_{666,14}$-2EH following the extraction procedure outlined above. Results are presented in Table 17.

TABLE 17

Partitioning of Propionic Acid in NIO Solvents and $P_{666,14}$-2EH (40° C.)

| Solvent | $P_{cont}$ | Propionic Acid at $P_{cont}$ (wt %) | $R_{extr}$ | Extraction Factor (ε) |
|---|---|---|---|---|
| MTBE | 3.2 | 20.2 | 0.30 | 10.7 |
| MIBK | 2.6 | 18.8 | 0.46 | 5.5 |
| BuOAc | 2.0 | 17.7 | 0.30 | 6.50 |
| $P_{666,14}$-2EH | 7.64 | 25.1 | 0.16 | 47.3 |

Example 18

Extraction of n-Butyric Acid with NIO Solvents Compared to $P_{666,14}$-2EH

This example presents extraction factors for the extraction of n-butyric acid with NIO solvents MTBE, MIBK, and n-butyl acetate, and $P_{666,14}$-2EH following the extraction procedure outlined above. Results are presented in Table 18.

TABLE 18

Partitioning of n-Butyric Acid in NIO Solvents and $P_{666,14}$-2EH (40° C.)

| Solvent | $P_{cont}$ | Butyric Acid at $P_{cont}$ (wt %) | $R_{extr}$ | Extraction Factor (ε) |
|---|---|---|---|---|
| MTBE | 9.9 | 25.2 | 0.20 | 48.5 |
| MIBK | 8.4 | 23.0 | 0.31 | 27.3 |
| BuOAc | 6.8 | 22.1 | 0.22 | 30.9 |
| $P_{666,14}$-2EH | 4.6 | 22.0 | 0.17 | 27.0 |

Example 19

Extraction of Acrylic Acid with NIO Solvents Compared to $P_{666,14}$-2EH

This example presents extraction factors for the extraction of acrylic acid with NIO solvents MTBE, MIBK, and n-butyl acetate, and $P_{666,14}$-2EH following the extraction procedure outlined above. Results are presented in Table 19.

TABLE 19

Partitioning of Acrylic Acid in NIO Solvents and $P_{666,14}$-2EH (40° C.)

| Solvent | $P_{cont}$ | Acrylic Acid at $P_{cont}$ (wt %) | $R_{extr}$ | Extraction Factor (ε) |
|---|---|---|---|---|
| MTBE | 3.6 | 24.2 | 0.31 | 11.8 |
| MIBK | 2.7 | 21.6 | 1.40 | 6.8 |
| BuOAc | 2.1 | 20.6 | 0.30 | 6.9 |
| $P_{666,14}$-2EH | 4.8 | 20.9 | 0.17 | 28.5 |

The invention has been described in detail with particular reference to preferred embodiments thereof, but it will be understood that variations and modifications can be effected within the spirit and scope of the invention.

We claim:

1. A composition for separating a $C_1$ to $C_4$ carboxylic acid from water, the composition comprising:
   (a) a quaternary phosphonium carboxylate salt;
   (b) a hydrophobic non-ionic organic solvent;
   (c) a $C_1$ to $C_4$ carboxylic acid; and
   (d) water,
   wherein the hydrophobic non-ionic organic solvent is not the extract, and
   wherein the carboxylate salt has the general formula 1:

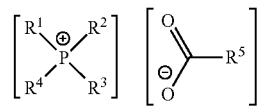

1 wherein
$R^1$, $R^2$, $R^3$ and $R^4$ are each independently a $C_1$ to $C_{26}$ hydrocarbyl group, provided that $R^1$, $R^2$, $R^3$, and $R^4$ collectively have a total of at least 24 carbon atoms; and
$R^5$ is hydrogen or a $C_1$ to $C_{24}$ non-aromatic hydrocarbyl group.

2. The composition according to claim 1, wherein the carboxylate salt comprises a tetraalkylphosphonium salt of formic acid, acetic acid, propionic acid, n-butyric acid, isobutyric acid, n-valeric acid, isovaleric acid, n-hexanoic acid, 2-ethylbutyric acid, heptanoic acids, n-octanoic, 2-ethylhexanoic acid, nonanoic acid, decanoic acid, dodecanoic acid, palmitic acid, stearic acid, oleic acid, linolenic acid, mixed vegetable-derived acids, or chloroacetic acid.

3. The composition according to claim 1, wherein the carboxylate salt comprises a trihexyl(tetradecyl)phosphonium salt of formic acid, acetic acid, propionic acid, n-butyric acid, isobutyric acid, n-valeric acid, isovaleric acid, n-hexanoic acid, 2-ethylbutyric acid, heptanoic acid, n-octanoic, 2-ethylhexanoic acid, nonanoic acid, decanoic acid, dodecanoic acid, palmitic acid, stearic acid, oleic acid, linolenic acid, mixed vegetable-derived acids, or chloroacetic acid.

4. The composition according to claim 1, wherein the carboxylate salt comprises trihexyl(tetradecyl)phosphonium carboxylate.

5. The composition according to claim 1, which comprises at least two of the carboxylate salts.

6. The composition according to claim 1, wherein the hydrophobic non-ionic organic solvent is selected from the group consisting of higher carboxylic acids, ethers, esters, ketones, aromatic hydrocarbons, chlorinated hydrocarbons, and nitriles.

7. The composition according to claim 6, wherein the hydrophobic non-ionic organic solvent comprises a higher carboxylic acid.

8. The composition according to claim 7, wherein the higher carboxylic acid is selected from the group consisting of n-butyric acid, isobutyric acid, n-valeric acid, isovaleric acid, n-hexanoic acid, 2-ethylbutyric acid, heptanoic acid, n-octanoic, 2-ethylhexanoic acids, nonanoic acids, decanoic acids, dodecanoic acids, stearic acid, oleic acid, linolenic acid, and mixed vegetable-derived acids.

9. The composition according to claim 8, wherein the higher carboxylic acid is selected from the group consisting of n-butyric acid, isobutyric acid, n-valeric acid, isovaleric acid, n-hexanoic acid, 2-ethylbutyric acid, heptanoic acid, n-octanoic acid, and 2-ethylhexanoic acid.

10. The composition according to claim 1, wherein the hydrophobic non-ionic organic solvent is selected from the group consisting of esters containing four to six carbon atoms, ketones containing five to nine carbon atoms, and ethers containing four to eight carbon atoms.

11. The composition according to claim 10, wherein the hydrophobic non-ionic organic solvent is selected from the group consisting of ethyl acetate, n-propyl acetate, n-propyl formate, i-propyl acetate, i-propyl formate, n-butyl acetate, n-butyl formate, i-butyl acetate, i-butyl formate, n-propyl propionate, i-propyl propionate, 2-pentanone, 3-pentanone, methyl isobutyl ketone, 3-methyl-2-butanone, 2-hexanone, 2-heptanone, cyclohexanone, 4-methyl-2-pentanone, 2,4-dimethyl-3-pentanone, 5-methyl-2-hexanone, 4-heptanone, 2-octanone, 5-nonanone, 2,8-dimethyl-4-heptanone, 3,3,5-trimethyl cyclohexanone, isophorone, diethyl ether, methyl propyl ether, dipropyl ether, di-isopropyl ether, methyl t-butyl ether, tertiary amyl methyl ether, ethyl butyl ether, toluene, m-xylene, p-xylene, and o-xylene.

12. The composition according to claim 11, wherein the hydrophobic non-ionic organic solvent is selected from the group consisting of methyl isobutyl ketone, toluene, isopropyl acetate, and methyl t-butyl ether.

13. The composition according to claim 1, which comprises at least two of the hydrophobic non-ionic organic solvents.

14. The composition according to claim 1, which comprises 10 to 90 weight percent of the carboxylate salt and 10 to 90 weight percent of the hydrophobic non-ionic organic solvent.

15. The composition according to claim 1, which comprises 50 to 90 weight percent of the carboxylate salt and 10 to 50 weight percent of the hydrophobic non-ionic organic solvent.

16. A process for separating a $C_1$ to $C_4$ carboxylic acid from water, the process comprising:
contacting a feed mixture comprising a $C_1$ to $C_4$ carboxylic acid and water with an extraction solvent comprising a quaternary phosphonium carboxylate salt and a non-ionic organic solvent at conditions effective to form (a) an extract mixture comprising the carboxylate salt, the non-ionic organic solvent, and at least a portion of the $C_1$ to $C_4$ carboxylic acid from the feed mixture and (b) a raffinate mixture comprising water and less of the $C_1$ to $C_4$ carboxylic acid compared to the feed mixture, wherein the non-ionic organic solvent is not the extract, and
wherein the carboxylate salt has the general formula 1:

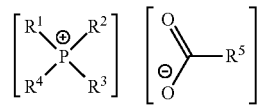

wherein
$R^1$, $R^2$, $R^3$ and $R^4$ are each independently a $C_1$ to $C_{26}$ hydrocarbyl group, provided that $R^1$, $R^2$, $R^3$, and $R^4$ collectively have a total of at least 24 carbon atoms; and
$R^5$ is a $C_1$ to $C_{20}$ non-aromatic hydrocarbyl group.

17. The process according to claim 16, wherein the carboxylate salt comprises a tetraalkylphosphonium salt of formic acid, acetic acid, propionic acid, n-butyric acid, isobutyric acid, n-valeric acid, isovaleric acid, n-hexanoic acid, 2-ethylbutyric acid, heptanoic acids, n-octanoic, 2-ethylhexanoic acid, nonanoic acid, decanoic acid, dodecanoic acid, palmitic acid, stearic acid, oleic acid, linolenic acid, mixed vegetable-derived acids, or chloroacetic acid.

18. The process according to claim 16, wherein the carboxylate salt comprises trihexyl(tetradecyl)phosphonium carboxylate.

19. The process according to claim 16, wherein the extraction solvent comprises at least two of the carboxylate salts.

20. The process according to claim 16, wherein the non-ionic organic solvent is selected from the group consisting of higher carboxylic acids, ethers, esters, ketones, aromatic hydrocarbons, chlorinated hydrocarbons, and nitriles.

21. The process according to claim 20, wherein the higher carboxylic acid is selected from the group consisting of n-butyric acid, isobutyric acid, n-valeric acid, isovaleric acid, n-hexanoic acid, 2-ethylbutyric acid, heptanoic acid, n-octanoic, 2-ethylhexanoic acids, nonanoic acids, decanoic acids, dodecanoic acids, stearic acid, oleic acid, linolenic acid, and mixed vegetable-derived acids.

22. The process according to claim 20, wherein the non-ionic organic solvent is selected from the group consisting of ethyl acetate, n-propyl acetate, n-propyl formate, i-propyl acetate, i-propyl formate, n-butyl acetate, n-butyl formate, i-butyl acetate, i-butyl formate, n-propyl propionate, i-propyl propionate, 2-pentanone, 3-pentanone, methyl isobutyl ketone, 3-methyl-2-butanone, 2-hexanone, 2-heptanone, cyclohexanone, 4-methyl-2-pentanone, 2,4-dimethyl-3-pentanone, 5-methyl-2-hexanone, 4-heptanone, 2-octanone, 5-nonanone, 2,8-dimethyl-4-heptanone, 3,3,5-trimethyl cyclohexanone, isophorone, diethyl ether, methyl propyl ether, dipropyl ether, di-isopropyl ether, methyl t-butyl ether, tertiary amyl methyl ether, ethyl butyl ether, toluene, m-xylene, p-xylene, and o-xylene.

23. The process according to claim 16, wherein the extraction solvent comprises at least two of the non-ionic organic solvents.

24. The process according to claim 16, wherein the extraction solvent comprises 10 to 90 weight percent of the carboxylate salt and 10 to 90 weight percent of the non-ionic organic solvent.

25. The process according to claim 16, wherein the $C_1$ to $C_4$ carboxylic acid comprises acetic acid.

26. The process according to claim 16, wherein the feed mixture comprises at least two of the $C_1$ to $C_4$ carboxylic acids.

27. The process according to claim 16, wherein the feed mixture comprises 0.5 to 60 weight percent of the $C_1$ to $C_4$ carboxylic acid.

28. The process according to claim 16, wherein the feed mixture is derived from the production of cellulose esters.

29. The process according to claim 16, wherein the weight ratio of the extraction solvent to the feed mixture ranges from 0.2 to 10:1.

30. The process according to claim 16, which further comprises:
   separating the extract mixture from the raffinate mixture; and
   recovering the $C_1$ to $C_4$ carboxylic acid from the extract mixture by distillation at atmospheric pressure or lower.

* * * * *